(12) United States Patent
Dacquay

(10) Patent No.: US 8,585,631 B2
(45) Date of Patent: Nov. 19, 2013

(54) ACTIVE BIMODAL VALVE SYSTEM FOR REAL-TIME IOP CONTROL

(75) Inventor: Bruno Dacquay, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 38 days.

(21) Appl. No.: 13/275,711

(22) Filed: Oct. 18, 2011

(65) Prior Publication Data

US 2013/0096483 A1  Apr. 18, 2013

(51) Int. Cl.
*A61B 19/00* (2006.01)
(52) U.S. Cl.
USPC .................................... 604/9; 604/8
(58) Field of Classification Search
USPC ........................................... 604/8, 9
See application file for complete search history.

(56) References Cited

U.S. PATENT DOCUMENTS

| | | | |
|---|---|---|---|
| 4,089,329 A | 5/1978 | Couvillon et al. |
| 4,206,762 A | 6/1980 | Cosman |
| 4,457,757 A | 7/1984 | Molteno |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters et al. |
| 5,005,577 A | 4/1991 | Frenkel |
| 5,083,742 A | 1/1992 | Wylie et al. |
| 5,178,604 A | 1/1993 | Baerveldt |
| 5,179,953 A | 1/1993 | Kursar |
| 5,397,300 A | 3/1995 | Baerveldt |
| 5,466,233 A | 11/1995 | Weiner et al. |
| 5,476,445 A | 12/1995 | Baerveldt |
| 5,558,629 A | 9/1996 | Baerveldt |
| 5,573,646 A | 11/1996 | Saito et al. |
| 5,626,558 A | 5/1997 | Suson |
| 5,681,275 A | 10/1997 | Ahmed |
| 5,707,643 A | 1/1998 | Ogura et al. |
| 5,910,110 A | 6/1999 | Bastable |
| 6,007,511 A | 12/1999 | Prywes |
| 6,048,328 A | 4/2000 | Haller et al. |
| 6,251,090 B1 | 6/2001 | Avery et al. |
| 6,447,449 B1 | 9/2002 | Fleischman et al. |

(Continued)

FOREIGN PATENT DOCUMENTS

| DE | 4438201 | 5/1996 |
|---|---|---|
| EP | 2427097 | 3/2012 |

(Continued)

OTHER PUBLICATIONS

International Searching Authority, International Search Report of the International Searching Authority, PCT/US2010/047612, Dec. 21, 2010, 7 pages.

(Continued)

*Primary Examiner* — Leslie Deak
(74) *Attorney, Agent, or Firm* — Kenneth D. Bassinger

(57) ABSTRACT

An IOP control system provides drainage from an anterior chamber of the eye to a drainage location at the eye. The system has a valve with an open flow position and a closed zero flow position. A sensor system includes a first sensor arranged to detect a first pressure representative of IOP. A controller receives data representing the detected pressure from the sensor system and compares the data to an upper pressure threshold and a lower pressure threshold to determine whether to change the state of the valve system in a bimodal fashion.

21 Claims, 4 Drawing Sheets

(56) References Cited

U.S. PATENT DOCUMENTS

| | | |
|---|---|---|
| 6,468,283 B1 | 10/2002 | Richter et al. |
| 6,579,235 B1 | 6/2003 | Abita et al. |
| 6,589,198 B1 | 7/2003 | Soltanpour et al. |
| 6,682,500 B2 * | 1/2004 | Soltanpour et al. ............... 604/9 |
| 6,712,764 B2 | 3/2004 | Jeffries et al. |
| 6,719,750 B2 | 4/2004 | Varner et al. |
| 6,749,568 B2 | 6/2004 | Fleischman et al. |
| 6,939,299 B1 | 9/2005 | Petersen et al. |
| 6,976,982 B2 | 12/2005 | Santini, Jr. et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,544,176 B2 * | 6/2009 | Rodgers et al. ................... 604/9 |
| 7,612,328 B2 | 11/2009 | Kaiser |
| 7,756,559 B2 | 7/2010 | Abreu |
| 7,824,699 B2 | 11/2010 | Ralph et al. |
| 8,182,435 B2 | 5/2012 | Dacquay et al. |
| 8,257,295 B2 | 9/2012 | Rickard et al. |
| 8,419,673 B2 | 4/2013 | Rickard |
| 2001/0000527 A1 | 4/2001 | Yaron et al. |
| 2002/0049374 A1 | 4/2002 | Abreu |
| 2002/0087111 A1 | 7/2002 | Ethier et al. |
| 2002/0099359 A1 | 7/2002 | Santini, Jr. et al. |
| 2002/0139947 A1 | 10/2002 | Wang |
| 2002/0143284 A1 | 10/2002 | Tu et al. |
| 2002/0193674 A1 | 12/2002 | Fleischman et al. |
| 2003/0014036 A1 | 1/2003 | Varner et al. |
| 2003/0078487 A1 | 4/2003 | Jeffries |
| 2003/0225318 A1 | 12/2003 | Montegrande et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0077270 A1 | 4/2007 | Wen |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0212397 A1 | 9/2007 | Roth |
| 2008/0015421 A1 | 1/2008 | Penner |
| 2008/0027478 A1 | 1/2008 | Connors et al. |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2009/0069648 A1 | 3/2009 | Irazoqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0240215 A1 | 9/2009 | Humayun et al. |
| 2009/0275924 A1 * | 11/2009 | Lattanzio et al. .......... 604/891.1 |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121248 A1 | 5/2010 | Yu et al. |
| 2010/0174272 A1 | 7/2010 | Weiner |
| 2010/0222769 A1 | 9/2010 | Meng et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegmann et al. |
| 2011/0071456 A1 | 3/2011 | Rickard |
| 2011/0071505 A1 * | 3/2011 | Rickard et al. ................ 604/540 |
| 2011/0248671 A1 | 10/2011 | Santos et al. |

FOREIGN PATENT DOCUMENTS

| | | |
|---|---|---|
| WO | 93/03665 | 3/1993 |
| WO | 9803809 | 1/1998 |
| WO | WO 98/03665 | 1/1998 |
| WO | WO 99/38470 A2 | 8/1999 |
| WO | WO 99/38470 A3 | 10/1999 |
| WO | 02056758 | 7/2002 |
| WO | 03/001991 | 1/2003 |
| WO | WO 03/102632 | 12/2003 |
| WO | 2005088417 | 9/2005 |
| WO | 2007/136993 | 11/2007 |
| WO | WO 2007/127305 A2 | 11/2007 |
| WO | WO 2008/061043 A2 | 5/2008 |
| WO | 2008084350 | 7/2008 |
| WO | WO 2008/061043 A3 | 9/2008 |
| WO | 2009010799 | 1/2009 |
| WO | 2009/026499 | 2/2009 |
| WO | 2009/049686 | 4/2009 |
| WO | WO 2009/081031 | 7/2009 |
| WO | WO 2009/081031 A3 | 9/2009 |
| WO | 2010/129446 A1 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |
| WO | 2012012017 | 1/2012 |

OTHER PUBLICATIONS

International Searching Authority, Written Opinion of the International Searching Authority, PCT/US2010/047612, Dec. 21, 2010, 10 pages.

International Searching Authority, Search Report of the International Searching Authority, PCT/US2011/036742, Aug. 17, 2011, 2 pages.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/049424, Nov. 26, 2010, 15 pages.

International Searching Authority, Written Opinion of the International Searching Authority, PCT/US2010/047605, Dec. 16, 2010, 9 pages.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(56) References Cited

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.
Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalinologica Scandinavica, 1995, pp. 5-11, vol. 73, Denmark.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matted, et al., "A Soft Contact Lens With a Mems Strain Gage Embedded for Intraocular Pressure Monitoring," in Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, p. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine."
Barton, Keith, et al., "The Ahmed Baerveldt Comparison Study," Journal of Ophthalmology, Jul. 15, 2010, vol. 118, No. 3,Elsevier, Inc., USA.
International Searching Authority, Search Report of the International Searching Authority, PCT/2012/057261, Jan. 23, 2013, 7 pages.
International Searching Authority, Written Opinion of the International Searching Authority, PCT/2012/057261, Jan. 23, 2013, 10 pages.
International Searching Authority, International Search Report, PCT/US2013/026066, Apr. 17, 2013, 5 pages.
International Searching Authority, Written Opinion of the International Searching Authority, PCT/US2013/026066, Apr. 17, 2013, 8 pages.
International Searching Authority, Invitation to Pay Additional Fees and, Where Applicable, Protest Fee (Partial Search Report attached), PCT/US2012/067741, Apr. 2, 2013, 6 pages.
Driot et al.; "Ocular pharmacokinetics of fluocinolone acetonide after RetisertTM intravitreal implantation in rabbits over a 1-year period"; J. Ocular Pharm; 20; 3;pp. 269-275.
Glybina et al.; "Neuroprotective properties of fluocinolone acetonide chronically delivered into the vitreous of albino RCS rats"; IVOS; 47; ARVO e-Abstract 1028.
Kuppermann B D et al., 2006, "Efficacy and safety of a novel intravitreous dexamethasone drug-delivery system after applicator or incisional placement in patients with macular edema", IOVS, 47 ARVO E-Abs 5913.
Miyamoto H et al., 1997, Biodegradable scleral implant for intravitreal controlled release of fluconazole, Curr Eye Res, 16(9), 930-935.
Mruthyunjaya P et al., 2003, "An intravitreal sustained release fluocinolone acetonide device to treat severe experimental uveitis", IOVS, 44, ARVO E-Abs 4215.
Ratanapakorn T et al., 2005, "Helical intravitreal triamcinolone implant: An explanation survival study", IVOS 46 E-Abs 484.
Rego Mgr et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
See R F et al., 2006, "Safety and drug release profile of injectable intravitreal sustained-release fluocinolone acetonide device", IOVS, 47, ARVO E-Abs 5119.
Tano R et al., 2005, Helical intravitreal implant: surgical method development and outcomes, IOVS, 46, ARVO E-Abs 483.
Varner S E et al., 2003, "Development of a minimally invasive intravitreal implant for drug delivery", IOVS, 44, ARVO E-Abs 4214.
Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press, New York", pp. 7-43.
Yasukawa T et al., 2001, "Biodegradable scleral plugs for vitreoretinal drug delivery", Adv. Drug Del Rev., 52(1), 25-36.
International Searching Authority, Written Opinion of the International Searching Authority, PCT/US2012/068878, Mar. 3, 2013, 8 pages.
International Searching Authority, International Search Report, PCT/US2012/068878, Mar. 3, 2013, 5 pages.
International Searching Authority, International Search Report, PCT/US2012/067747, Apr. 2, 2013, 4 pages.
International Searching Authority, Written Opinion of the International Searcing Authority, PCT/US2012/067747, Apr. 2, 2013, 7 pages.

* cited by examiner

ACTIVE BIMODAL VALVE SYSTEM FOR REAL-TIME IOP CONTROL

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidicly coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases overtime. This development and progression of fibrosis reduces or eliminates flow from the anterior chamber, eliminating the capacity of the drainage device to affect IOP.

The system and methods disclosed herein overcome one or more of the deficiencies of the prior art.

SUMMARY

In one exemplary aspect, the present disclosure is directed to an IOP control system for implantation in an eye of a patient to provide drainage from an anterior chamber of the eye to a drainage location at the eye, comprising:
a valve system having an fully open flow position and a closed zero flow position, the open flow position permitting fluid flow through the valve system, the closed zero flow position substantially preventing fluid flow through the valve system;
a sensor system comprising a first sensor arranged to detect a first pressure representative of a real-time parameter of the eye; and
a controller arranged to receive data from the sensor system and compare data representing the detected pressure to a preestablished upper pressure threshold and a preestablished lower pressure threshold to determine whether to change the state of the valve system in a bimodal fashion from one of a fully open flow position and the closed zero flow position to the other of the fully open flow position and the closed zero flow position.

In another exemplary aspect, the present disclosure is directed to a method for treating glaucoma using an IOP control system. The method may include a step of receiving an input representing a target pressure range for an eye of a patient, the target pressure range having an upper pressure threshold and a lower pressure threshold the upper and lower thresholds being extreme ends of the range of the target pressure range. The method may also include steps of detecting with at least one pressure sensor an actual pressure associated with the eye of a patient, comparing the actual pressure to the target pressure range, and actuating a valve in a bimodal manner between a drainage flow-permitting condition and a drainage flow-preventing condition based on the comparison of the actual pressure to the target pressure range.

In another exemplary aspect, the present disclosure is directed to an IOP control system for implantation in an eye of a patient to provide drainage from an anterior chamber of the eye to a drainage location at the eye. The system may include a bimodal valve system having an open flow position and a closed zero flow position. The open flow position may permit fluid flow through the valve system, and the closed position may substantially prevent fluid flow through the valve system. The system may also comprise a sensor system that includes a first sensor arranged to detect a first pressure representative of a real-time parameter of the eye and a second sensor arranged to detect a second pressure. A controller may be arranged to compare data representing the first and second pressures to a preestablished upper pressure threshold and a preestablished lower pressure threshold to determine whether to change the state of the valve system in a bimodal fashion between the open position and the closed position.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and method disclosed herein and together with the description, serve to explain the principles of the present disclosure.

DETAILED DESCRIPTION OF THE PREFERRED EMBODIMENTS

Figure 1:
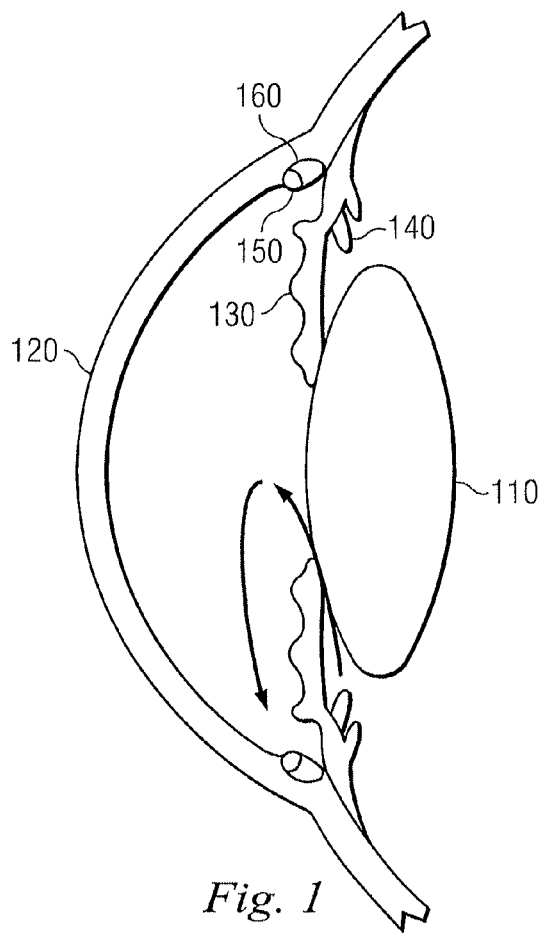
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

Prior efforts to control IOP with implantable valves fall primarily into two general categories. The first is a free-flow or uncontrolled drainage flow category, and the second is a microcontrolled drainage flow category. The free-flow category includes implant systems that provide continuous, unrestricted drainage from the anterior chamber. While suitable for draining fluid to reduce pressures in the anterior chamber, these devices are not able to close to reduce or prevent flow. The microcontrolled drainage flow category includes implant systems that utilize valves continuously controlled through variable settings to increase and decrease flow to achieve a target IOP value.

This disclosure is directed to a bimodal IOP control system. Being bimodal, it operates a flow control valve system in only two modes—a fully open flow mode and a closed or zero-flow mode. Here, fully open means a highest flow setting. It may coincide with the maximum flow rating of the valve or may be a maximum flow setting established by the operator or manufacturer. Here, the time history of the valve system is varied in order to maintain the IOP within a desired range. In other words, to raise or lower the IOP, the system disclosed herein varies the open/closed duty cycle of the valve system. The valve system is actuated only when one of the extreme limits of the desired IOP range is exceeded. When that occurs, the valve system is controlled in the bimodal manner from one setting to the other, such as from open to closed, or vice versa. Such a system may consume less power than prior devices because there are fewer adjustments. This may directly result in a device that is more reliable, more robust, and may require less maintenance.

Figure 2:
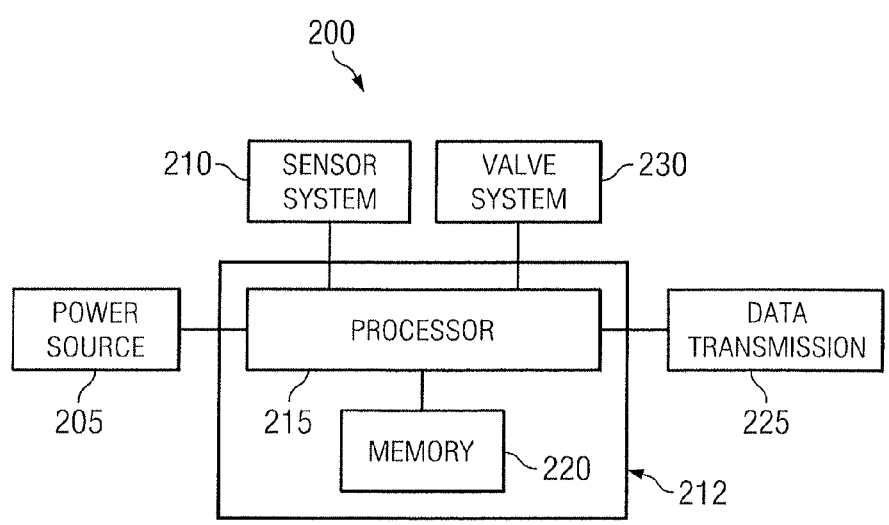
FIG. 2 is a block diagram of an exemplary IOP control system according to the principles of the present disclosure.

FIG. 2 is a block diagram of an exemplary IOP control system 200 implantable in an eye of a patient for the treatment of glaucoma or other conditions. The IOP control system 200 includes a power source 205, an IOP sensor system 210, a controller 212, a data transmission module 225, and a valve system 230.

The power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source can be recharged via inductive coupling such as an RFID link or other type of magnetic coupling.

The controller 212 comprises a processor 215 and a memory 220. It is configured to receive data, perform functions, and execute programs stored on the memory 220. In this case, the controller 212 is configured to operate the valve system 230 in a bimodal manner, where the controller is configured to control the valve system to operate in two conditions only: a fully open flow condition and a zero flow condition.

The processor 215 is typically an integrated circuit with power, input, and output pins capable of performing logic functions. In various embodiments, processor 215 is a targeted device controller. In such a case, the processor 215 performs specific control functions targeted to a specific device or component, such as a data transmission module 225, the power source 205, the sensing system 210, the valve system 230, or the memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

The memory 220 is typically a semiconductor memory such as RAM, FRAM, or flash memory. The memory 220 interfaces with the processor 215. As such, the processor 215 can write to and read from memory 220. For example, the processor 215 can be configured to read data from the IOP sensor system 210 and write that data to the memory 220. In this manner, a series of IOP readings can be stored in the memory 220. The processor 215 is also capable of performing other basic memory functions, such as erasing or overwriting the memory 220, detecting when the memory 220 is full, and other common functions associated with managing semiconductor memory.

The data transmission module 225 may employ any of a number of different types of data transmission. For example, data transmission module 225 may be an active device such as a radio, or may also be a passive device such as the antenna on an RFID tag. In such a case, an RFID tag may include the memory 220, while the data transmission module 225 is in the form of an antenna. An RFID reader placed near the system 200 may write data to or read data from memory 220. Since the amount of data typically stored in the memory 220 is likely to be small (consisting of IOP readings over a period of time), the speed with which data is transferred is not crucial. Other types of data that can be stored in the memory 220 and transmitted by the data transmission module 225 include, but are not limited to, power source data (e.g. low battery, battery defect), speaker data (warning tones, voices), IOP sensor data (IOP readings, problem conditions), time stamp data and the like.

Alternatively, the data transmission module 225 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), the processor 215 can read IOP measurements detected by the sensor system 210. If the processor 215 reads an unsafe IOP condition, data transmission module 225 can alert the patient and medical staff directly or by transmitting the unsafe readings to a secondary device.

Figure 3:
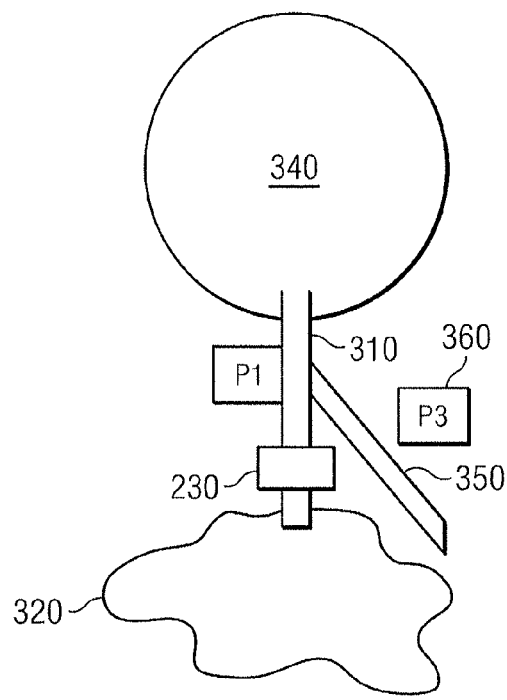
FIG. 3 is a diagram of an exemplary IOP control system according to the principles of the present disclosure.

FIG. 3 is a diagram of the exemplary IOP control system 200 with its sensor system 210, a drainage tube 310, the valve system 230, and a divider 350. The IOP control system 200 may be positioned within the eye in the subconjunctival pocket between the conjunctiva and the sclera with the anterior border of the IOP control system 200 positioned approximately 10 millimeters posterior to the limbus (the border between the cornea and the sclera). It may be held in place within the eye via anchoring structures, the angle of implantation and surrounding anatomy, or by a spring force or other mechanisms that stabilize the IOP control system 200.

In FIG. 3, the exemplary IOP sensor system 210 includes two pressure sensors, P1 and P3. Pressure sensor P1 is located in or is in fluidic communication with the anterior chamber 340, and pressure sensor P3 is located remotely from P1 in manner to measure atmospheric pressure. In some embodiments, pressure sensor P1 is located in a lumen or tube that is in fluid communication with the anterior chamber, such as in the drainage tube 310.

In the embodiment shown, the pressure sensor P1 measures the pressure in the tube 310 upstream from the valve system 230 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

The atmospheric pressure sensor P3 may be located in close proximity to the eye, and in one embodiment, is implanted in the eye under the conjunctiva. In such a case, pressure sensor P3 measures a pressure that can be correlated with atmospheric pressure. For example, true atmospheric pressure can be a function of the pressure reading of pressure sensor P3. As used herein, atmospheric pressure references include pressure references directly correlatable to atmospheric pressure. Pressure sensor P3 may also be located in a dry portion 360 of the subconjunctival space, separate from the drainage location. Regardless of location, pressure sensor P3 is intended to measure atmospheric pressure in the vicinity of the eye or at the eye's surface. In one embodiment having a standard GDD plate style shape, the pressure sensor P3 resides on the IOP with a barrier preventing it from being crushed while still allowing pressure communication through the conjunctiva.

Generally, IOP is a gauge pressure reading—the difference between the absolute pressure in the eye (as measured by P1) and atmospheric pressure (as measured by P3). Atmospheric pressure, typically about 760 mmHg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mmHg. Thus, for accurate monitoring of IOP, it is desirable to have pressure readings for the anterior chamber (as measured by P1) and atmospheric pressure in the vicinity of the eye (as measured by sensor P3).

Therefore, in one embodiment of the present invention, pressure readings are taken by P1 and P3 simultaneously or nearly simultaneously over time so that the actual IOP can be calculated (as P1−P3 or P1−f(P3), where f(P3) indicates a function of P3). The pressure readings of P1 and P3 can be stored in memory 220 by processor 215. They can later be read from memory so that actual IOP over time can be interpreted by a physician. Pressure sensors P1 and P3 can be any type of pressure sensors suitable for implantation in the eye. They each may be the same type of pressure sensor, or they may be different types of pressure sensors.

The divider 350 is a physical structure that separates the wet drainage site 320 from the pressure sensor P3. Divider 350 is included when the system of the present invention is located on a single substrate. In this configuration, both pressure sensors (P1 and P3) are located on a substrate that includes the tube 310, the valve system 230, the divider 350, and the other components of the system.

The drainage tube 310 may be arranged to shunt fluid from the anterior chamber 340 to a drainage location 320, which may at any of numerous locations within the eye. For example, some tubes are arranged to shunt aqueous from the anterior chamber 340 to the subconjunctival space thus forming a bleb under the conjunctiva or alternatively, to the subscleral space thus forming a bleb under the sclera. Other tube designs shunt aqueous from the anterior chamber to the suprachoroidal space, the supraciliary space, the juxta-uveal space, or to the choroid, forming blebs in those respective locations. In other applications, the drainage tube shunts aqueous from the anterior chamber to Schlemm's canal, a collector channel in Schlemm's canal, or any of a number of different blood vessels like an episcleral vein. In some examples, the drainage tube even shunts aqueous from the anterior chamber to outside the conjunctiva. Each of these different anatomical locations to which aqueous is shunted is an example of a drainage location 320. Other examples of a drainage location 320 include, but are not limited to: a subconjunctival space, a suprachoroidal space, a subscleral space, a supraciliary space, Schlemm's canal, a collector channel, an episcleral vein, and a uveo-scleral pathway.

Figure 4:
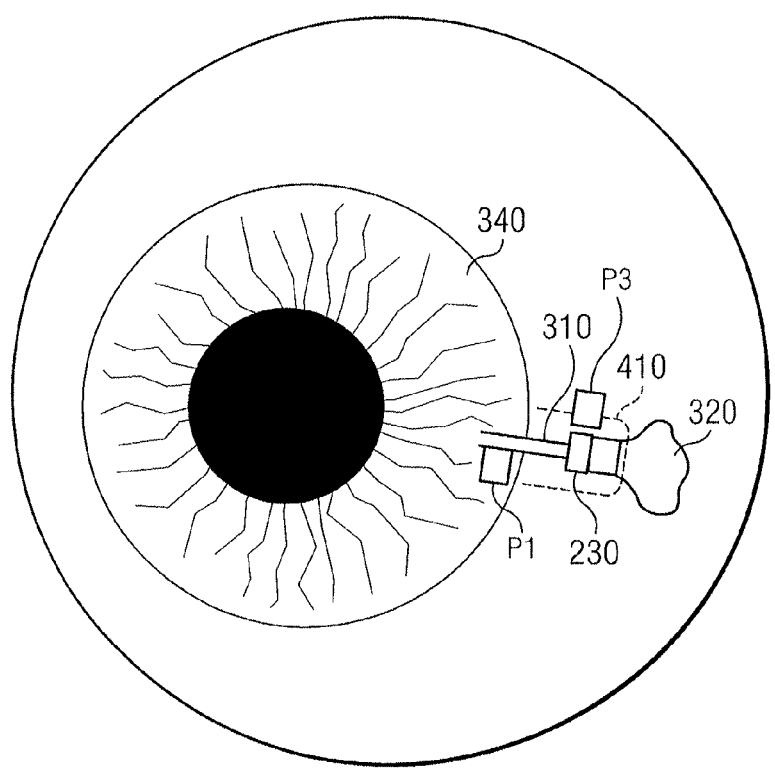
FIG. 4 is a diagram of one possible application of the IOP sensor of the present disclosure.

In FIG. 4, the tube 310 is located with one end in the anterior chamber 340 and the other end in the drainage location 320. The valve system 230 controls the flow of aqueous through the tube 310 from the anterior chamber 340 to drainage location 320. As indicated above, the pressure sensor P1 is located in the anterior chamber or in fluid communication with the anterior chamber 340, and therefore, as shown in the embodiment of FIG. 3, pressure sensor P1 is located upstream from valve system 230.

The IOP control system 200 controls IOP so that it stays within an acceptable range or acceptable parameters while minimizing actual adjustment. Readings from pressure sensors P1 and P3 can be used as inputs relied upon to control fluid flow rates through tube 310 by controlling the valve system 230. In this manner, IOP is the control parameter. To accomplish this, the valve system 230 adjusts to maintain the IOP within a particular pressure range (like an IOP pressure of 10-20 mm Hg). In one example, the IOP pressure range includes upper and lower thresholds, with the IOP upper pressure threshold being in the range of about 15 to 18 mmHg and the IOP lower pressure threshold being in the range of about 8 to 10 mmHg. Note that in some embodiments, the physician is able to determine and program the high/low IOP thresholds to meet each patient's specific requirements. This may be done with an input interface, such as a keyboard or other input device. In other embodiments, the thresholds are preset during manufacturing.

The valve system 230 may be controlled by the controller 212 based on input data received from the sensors P1, P3. A desired pressure differential (that corresponds to a desired flow rate) can be maintained by controlling the operation of valve system 230. Likewise, a desired IOP, IOP change rate, or bleb pressure can be controlled by controlling the operation of valve system 230.

Figure 5:
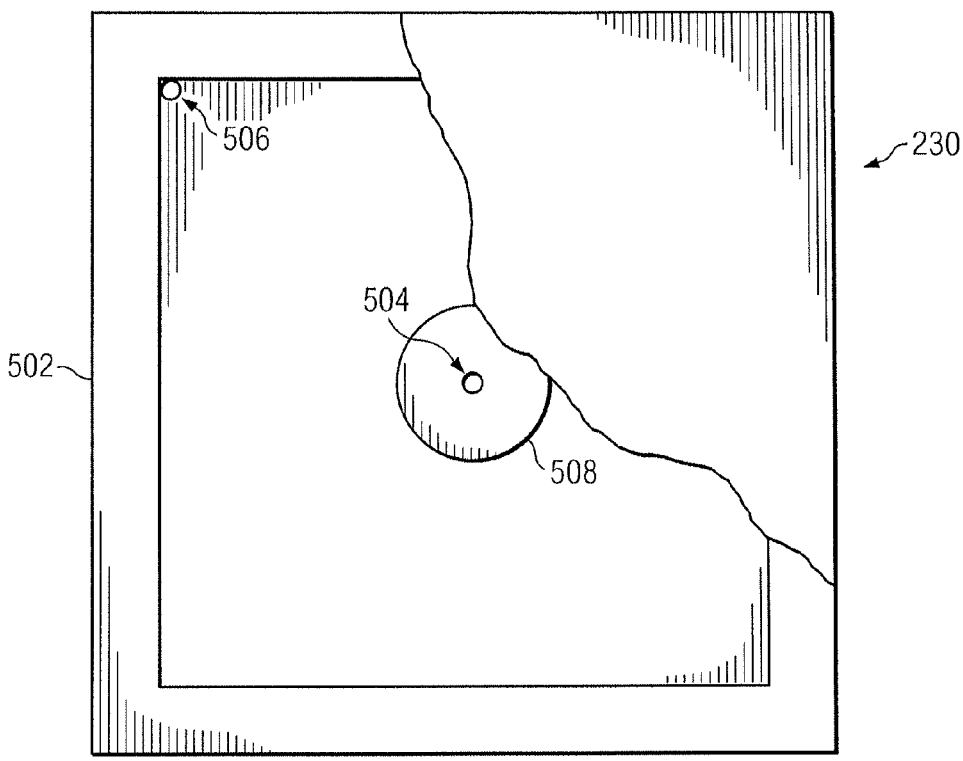
FIGS. 5-7 are illustrations of a cross-sectional view of an exemplary valve system according to one embodiment consistent with the principles of the present disclosure.

FIG. 5 shows an exemplary embodiment of the valve system 230 in greater detail. The valve system 230 is disposed along, and may form a part of, the drainage tube 310 between the tube end in the anterior chamber and the tube end at the drainage site. It may be configured to control the flow of drainage fluid through the drainage tube 310, and thereby control pressure in the eye, including the IOP. For example, when IOP is high, the valve system 230 may operate in a first mode to permit a maximum flow through the drainage tube, and when IOP is low, the valve system 230 may operate in a second mode to prevent the flow through the drainage tube. To accomplish this, the valve system 230 is responsive to signals sent as instructions from the processor 215. The processor 215 is responsive to pressure measurements taken by the pressure sensors P1, P3, and/or the IOP as determined by detected pressures, as explained above. In another embodiment, a pressure sensor, P2, is located in or in fluidic communication with the drainage location 320 and thus measurements taken by P2 and P3 can also influence response from valve system 230. For example, if the IOP (P1–P3) is high but the drainage pressure location (P2–P3) is also high, valve system 230 may delay opening until the drainage site pressure naturally reduced. In one example, the drainage site pressure range includes an upper pressure threshold being in the range of about 12 to 15 mmHg.

Figure 6:
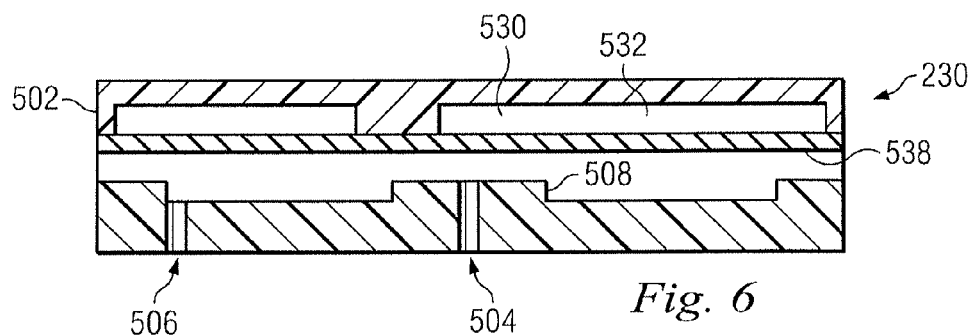
Figure 7:
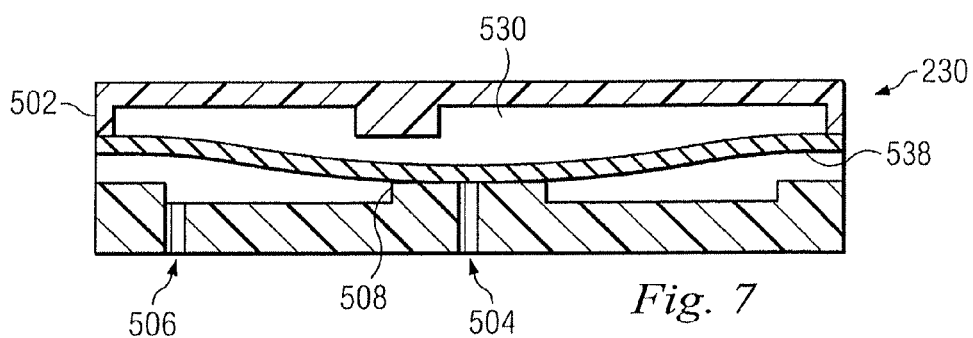

FIGS. 5-7 show an exemplary valve system 230 according to an embodiment of the present disclosure. More specifically, FIG. 5 is a diagrammatic IOP view of the valve system 230; FIG. 6 is a diagrammatic cross-sectional side view of the valve system 230 in a fully open flow condition; and FIG. 7 is a diagrammatic cross-sectional side view of the valve system 230 similar to that of FIG. 6, but showing the valve system 230 in a fully closed or zero flow condition.

As shown in FIGS. 5-7, the valve system 230 includes a housing 502 with an entrance port 504 and an exit port 506, a boss 508, and a flow control system 510. The entrance port 504 connects to the drainage tube 310 and is configured to receive aqueous flowing from the drainage tube 310. The exit port 506 permits aqueous to exit the housing 502 for release at the drainage site 320 or for further regulation.

In one embodiment, the flow control system 510 includes a flow control chamber 530, an actuator fluid 532 in the flow control chamber 530, electrodes (not shown) arranged to cooperate with the actuator fluid 532, and a flexible membrane 538. In operation the electrodes (not shown) generate bubbles in the actuator fluid 532 through electrolysis, increasing the volume and thus the pressure within the chamber of the flow control chamber 530. As the pressure increases, the flexible membrane 538 expands toward the boss 508, decreasing and ultimately preventing fluid flow from the entrance port 504, thereby restricting aqueous flow from the drainage tube 310. In a similar, but opposite manner, as the solution in the flow control chamber 530 returns to its more fluid state, the volume in the chamber 530 decreases, permitting the flexible membrane 538 to move away from the boss 508, thereby permitting aqueous to flow from the drainage tube 310 through the valve system 230.

As can be seen in FIG. 5, in the example shown, the flow control chamber is formed in the housing 502 with rigid structure formed by the housing walls on three sides. The chamber 530 is sealed closed by the flexible membrane 538. Accordingly, as volume increases, the pressure increase acts to displace the membrane 538 in only one direction.

The flexible membrane 538 may be formed of an elastically deformable elastomeric including without limitation, materials such as a silicone, silicone nitride, silicone elastomeric, polyimide, parylene and others. In the example shown, the flexible membrane 538 is secured to the housing 502 at its edges. In the embodiment shown, the flexible membrane 538 is formed as a square shaped structure. In other embodiments however the valve system 230, including the flexible membrane 538, may be a circular material secured at its periphery to the housing 502. As such, as the volume or pressure increases within the chamber, the central portion of the flexible membrane provides the highest level of displacement. In other embodiments, the housing and flexible membrane are formed so that the membrane has a non-circular shape, including oval, substantially rectangular, or square, for example. Other shapes are also contemplated. Applicable to all flexible membranes such as 538 may also have corrugation features (such as ridges and valleys), whose depths will effect the displacement shape. For example, deep corrugations would lead to greater displacement, whereas shallow corrugations would lead to smaller displacements. The placement of the shallow and deep corrugations may be used to create displacement shapes that are very steep then gradual or vices verse, this would allow for a greater control in the degree of pressure drop across the membrane at various displacement pressures allowing for an optimized design.

The actuator fluid 532 is contained in the flow control chamber 530 and, in some embodiments, includes water. Some embodiments include a saline like sodium chloride in the water.

The electrodes (not shown) are disposed within the actuator fluid 532 in a manner permitting at least a portion of the ions and electrolytes in the actuator fluid 532 to phase change from liquid to gas, forming the bubbles through electrolysis. As this occurs, the pressure in the chamber increases, thereby increasing overall pressure. This increased pressure acts on the flexible membrane 538 to cause its displacement. The electrodes are in electrical communication with the power source 205, which is controlled by the processor 215. Through the electrolysis, water in the actuator fluid 532 may result in hydrogen and oxygen molecules. The electrodes may be interdigitating electrodes for efficient and effective electrolysis.

In alternative embodiments, the flow control system 510 includes a mechanical displacement system that mechanically displaces the flexible membrane to regulate aqueous flow through the valve system. In one example, the mechanical displacement is a gear and rack system where displacement includes driving the gear. Other mechanical displacement systems are also contemplated. Other actuation mechanism are also contemplated, such as electromagnetic, electrostatic, piezoelectric, thermal, or shape-memory alloy.

Some embodiments of the valve system 230 include a latch (not shown) that enables the flexible membrane 538 to be secured and maintained in its displaced condition. The use of such a latch enables the flow through the valve system 230 to be modified, but then enables the position of the membrane to be maintained over time without the need for constant or intermittent power-consuming adjustments to maintain the volume or pressure in the flow control chamber 530. In some examples, the latch is a mechanical hook latch that captures the membrane and holds it in place until it is desired to be released. Accordingly, the latch may secure the flexible membrane in a position so that the passageway is in the open flow position or the closed zero flow position. This mechanical hook latch may be controlled and operated by the processor. In other examples, the latch is a mechanical displacement controlling the position of the edge of the membrane to move it relative to the passageway. Some embodiments use resistance or non-resistance latches. Some may require energy to disengage, but require no energy to engage. Some latches are biased with a spring constant biasing member.

Figure 8:
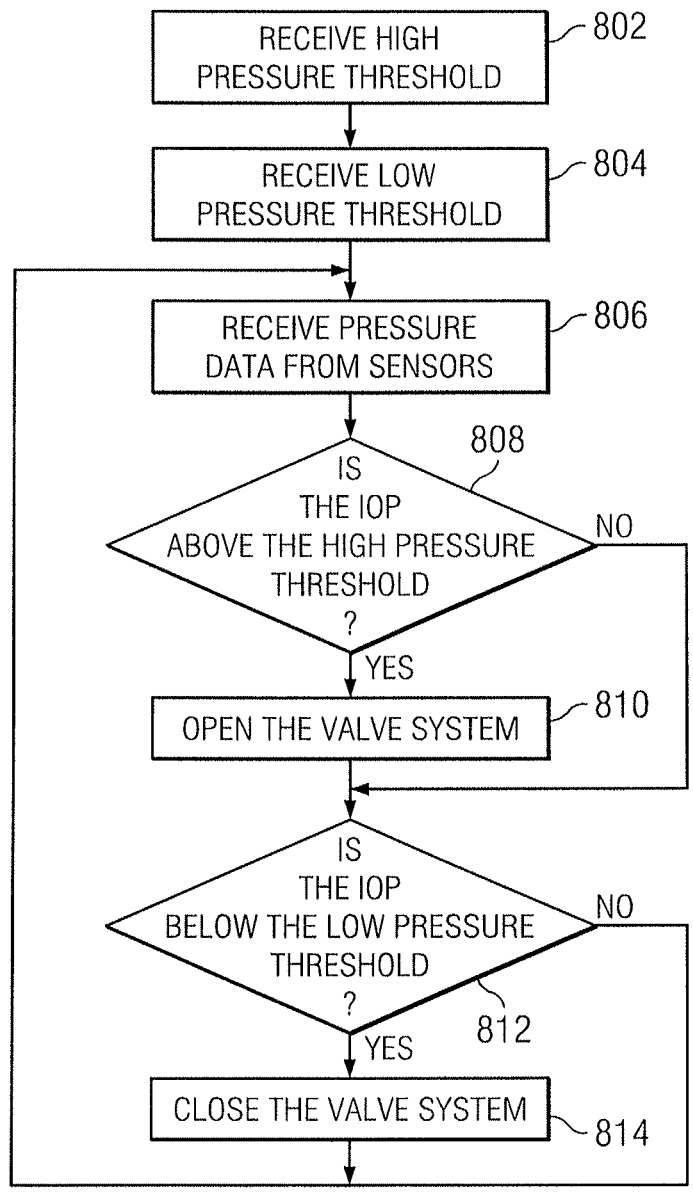
FIG. 8 is a flow chart illustrating a method of bimodal operation consistent with the principles of the present disclosure.

FIG. 8 illustrates an exemplary method performed by the IOP control system 200. The IOP control system 200 utilizes a general variable flow control valve that is particularly controlled to operate in a bimodal manner, meaning the valve is utilized in only two settings, a fully open flow setting and a zero-flow setting.

The method in FIG. 8 begins at a step 802 where the flow control system receives a high pressure threshold. In one embodiment, this high pressure threshold is received via the data transmission module 225 and stored in the memory 220. This high pressure threshold is stored as programming in the memory executable by the processor 215. In another example, high pressure threshold is a physical threshold created through an electronic filtering circuit that behaves in a desired manner when the pressure is measured to be above the high pressure threshold and behaves in different manner when the pressure is measured to be below the high pressure threshold. In some examples, the high pressure threshold is received from a health care provider, who may be the health care provider implanting the glaucoma treatment device or a health care provider customizing the implant to the specific needs of a patient. In other examples, the high pressure threshold is received during programming by the manufacturer or hard coded into the circuitry of the IOP control system 200 during manufacturing.

At a step 804, the flow control system receives a low pressure threshold. It may be entered or generated in the same manner as the high pressure threshold discussed above. That is, among other things, it may be inputted and stored by a health care provider or a manufacturer, it may be, for example, an electronic circuit, or it may be hard coded.

The high pressure threshold and the low pressure threshold together define the extreme limits of an acceptable pressure range for IOP. As discussed above, the IOP may be determined by the pressure measurements as the data collected by the pressure sensors P1 and P3 (or, alternatively, P2 and P3). In one example, instead of using IOP as the benchmark for the high and low pressure thresholds, the flow control system 200 is configured to operate entirely based on pressure readings from sensor P1, for example.

With the high and low thresholds established, the processor 215 receives data from the pressure sensors P1 and P3, at step 806 in real time. In some examples, to conserve power, data from the pressure sensors is collected only at preestablished intervals, such as, for example, in real time once every 20 minutes. Both longer and shorter intervals are contemplated. In other examples, data from the pressure sensors is continuously received in real time and processed at the processor 215, providing continuous assessment of the current pressures. The processor 215 may manipulate these measured pressures as discussed above to determine an IOP.

At a step 808, the processor 215 compares the pressure data to the high pressure threshold, and queries whether the IOP is above the high pressure threshold. If the IOP is above the high pressure threshold, then the processor 215 takes action to reduce the IOP to a level consistent with the desired target range. To do this, as indicated at step 810, the processor 215 generates and sends a control signal to the valve system 230 to open the valve system from a closed condition to an open position in a bimodal manner. If the valve is already opened, the valve simply remains open. Based on the signal received at the valve system 810, the valve system opens to its fully open flow setting. Since the valve operates in a bimodal manner, with a fully open flow setting and a closed or zero-flow setting, switching to the flow setting opens the valve to permit the maximum amount of flow obtainable by the IOP control system when it is operated in a bimodal manner.

If the IOP is not above the high pressure threshold at step 808, then the processor 215 compares the pressure data to the low pressure threshold, and queries whether the IOP is below the low pressure threshold at a step 812. If the IOP is below the low pressure threshold at a step 812, then the processor 215 takes action to increase the IOP to a level consistent with the desired target range. To do this, as indicated at step 814, the processor 215 generates and sends a control signal to the valve system 230 to close the valve system from an open condition to a closed condition. If the valve is already closed, the valve simply remains closed. Based on the signal received at the valve system 810, the valve system closes, preventing flow through the system. Since the valve operates in a bimodal manner, with a full flow setting and a zero-flow setting, switching to the flow setting to the zero flow blocks all drainage flow. Once the valve system 230 is closed, it will not reopen until the IOP increases and exceeds the high pressure threshold.

If the IOP is not below the low pressure threshold at step 812, then the processor 215 loops back to step 806 and again receives data from the pressure sensors P1 and P3 (or, alternatively, P2 and P3).

The high and low pressure thresholds are the extreme ends of the acceptable range of IOP pressures. By setting the thresholds at the extreme limits, actuation of the valve system from one mode to the other is delayed until necessary. This means that changes are minimized and occur only when necessary to maintain the pressures within the extreme limits, thereby conserving power and prolonging the life of the power supply, redoing the frequency of required maintenance, and increasing reliability of the IOP control system as a whole.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

I claim:

1. An IOP control system for implantation in an eye of a patient to provide drainage from an anterior chamber of the eye to a drainage location at the eye, comprising:
    a valve system having an open flow position and a closed zero flow position, the open flow position permitting fluid flow through the valve system, the closed zero flow position substantially preventing fluid flow through the valve system, the valve system comprising:
        a housing;
        a flexible membrane coupled with the housing, the flexible membrane having a first side and a second side;
        a chamber bounded by an interior of the housing and a first side of the flexible membrane, the chamber holding an actuation fluid;
        an entrance port and an exit port located in the housing adjacent to the second side of the flexible membrane;
        a passage located inside the housing, the passage fluidly coupling the entrance port to the exit port;
        wherein when the valve system is in the closed zero flow position, the flexible membrane occludes the entrance port;
    a sensor system comprising a first sensor arranged to detect a first pressure representative of a real-time parameter of the eye; and
    a controller arranged to receive data from the sensor system and compare data representing the detected pressure to a preestablished upper pressure threshold and a preestablished lower pressure threshold to determine whether to change the state of the valve system in a bimodal fashion from one of an open flow position and the closed zero flow position to the other of the open flow position and the closed zero flow position.

2. The IOP control system of claim 1, wherein the first sensor of the sensor system is arranged to detect the anterior chamber pressure.

3. The IOP control system of claim 2, wherein the sensor system comprises a second sensor arranged to detect the drainage site pressure.

4. The IOP control system of claim 3, wherein the sensor system comprises a third sensor arranged to detect an atmospheric pressure.

5. The IOP control system of claim 1, wherein the sensor system comprises a second sensor arranged to detect an atmospheric pressure, and
    wherein the controller is arranged to determine a value representative of IOP, the controller being arranged to compare the IOP to the upper and lower pressure thresholds.

6. The IOP control system of claim 5, wherein the controller is also arranged to determine a value representative of drainage site pressure, the controller being arranged to compare the IOP to the upper and lower pressure thresholds and arranged to compare the drainage site pressure to the upper pressure threshold.

7. The IOP control system of claim 6, wherein the upper pressure threshold for the drainage location is in the range of about 12-15 mmHg.

8. The IOP control system of claim 1, wherein the processor is configured to generate a signal to open the valve when the data representing the pressures is above the upper threshold.

9. The IOP control system of claim 8, wherein the processor is configured to generate a signal to close the valve when the data representing the pressures is below the lower threshold.

10. The IOP control system of claim 1, wherein the upper pressure threshold for IOP is in the range of about 15 to 18 mmHg and the lower pressure threshold is in the range of about 8 to 10 mmHg.

11. The IOP control system of claim 1, further comprising an interface arranged to receive an input from a health care provider establishing one of the upper pressure threshold and the lower pressure threshold.

12. The IOP control system of claim 1, wherein the controller is configured to generate and output a signal to the valve system to change from said one of the open flow position and the closed zero flow position to the other of the open flow position and the closed zero flow position.

13. The IOP control system of claim 1, wherein the controller is configured to monitor the data from the sensor system in real time.

14. The IOP control system of claim 1, wherein the controller and valve system are arranged so that the open condition coincides with the open flow condition for the valve system.

15. A method for treating glaucoma using an IOP control system, comprising:
    receiving an input representing a target pressure range for an eye of a patient, the target pressure range having an upper pressure threshold and a lower pressure threshold the upper and lower thresholds being extreme ends of the range of the target pressure range;
    detecting with at least one pressure sensor an actual pressure associated with the eye of a patient;
    comparing the actual pressure to the target pressure range; and
    actuating a valve in a bimodal manner between a drainage flow-permitting condition and a drainage flow-preventing condition based on the comparison of the actual pressure to the target pressure range;
    wherein actuating the valve in the drainage flow-preventing condition comprises performing electrolysis on an actuator fluid held in a chamber bounded by an interior of a valve housing and a side of a flexible membrane, such that a gas produced by electrolysis deflects the flexible membrane thereby occluding a port in the valve housing.

16. The method of claim 15, wherein the target pressure range for an eye of a patient is measured as an acceptable IOP range for the eye.

17. The method of claim 15, wherein the step of detecting with at least one pressure sensor comprises accounting for an anterior chamber pressure.

18. The method of claim 17, wherein the step of detecting with at least one pressure sensor further comprises accounting for an atmospheric pressure.

19. The method of claim 15, wherein receiving an input comprises receiving an input from one of a health care provider and a manufacturer.

20. The method of claim 15, wherein actuating a valve in a bimodal manner comprises opening the valve only when the comparison of the actual pressure to the target pressure range indicates that the pressure is greater than the upper pressure threshold.

21. The method of claim 15, wherein actuating a valve in a bimodal manner comprises closing the valve only when the comparison of the actual pressure to the target pressure range indicates that the pressure is less than the lower pressure threshold.

* * * * *